US009414830B2

(12) United States Patent
Marczyk et al.

(10) Patent No.: US 9,414,830 B2
(45) Date of Patent: Aug. 16, 2016

(54) SURGICAL ACCESS ASSEMBLY INCLUDING ADHESIVE MEMBERS FOR SECURE ATTACHMENT TO SKIN SURFACES

(71) Applicant: Covidien LP, Mansfield, MA (US)

(72) Inventors: Stanislaw Marczyk, Stratford, CT (US); Brian Rockrohr, Waterbury, CT (US); Christopher Switalski, Suffield, CT (US); Russell Pribanic, Roxbury, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/302,547

(22) Filed: Jun. 12, 2014

(65) Prior Publication Data

US 2014/0371537 A1    Dec. 18, 2014

Related U.S. Application Data

(60) Provisional application No. 61/834,937, filed on Jun. 14, 2013.

(51) Int. Cl.
*A61B 1/32* (2006.01)
*A61B 17/02* (2006.01)
*A61B 17/34* (2006.01)

(52) U.S. Cl.
CPC ......... *A61B 17/0218* (2013.01); *A61B 17/3421* (2013.01); *A61B 17/3439* (2013.01); *A61B 17/3462* (2013.01); *A61B 17/3474* (2013.01); *A61B 2017/3486* (2013.01); *A61B 2017/3492* (2013.01)

(58) Field of Classification Search
CPC .... A61B 2017/3492; A61B 17/3421–17/3462; A61B 17/02–17/0231; A61M 2025/0253; A61F 5/443
See application file for complete search history.

(56) References Cited

U.S. PATENT DOCUMENTS

| | | | |
|---|---|---|---|
| 2,389,355 A | 11/1945 | Goland et al. | |
| 3,670,727 A | 6/1972 | Reiterman | |
| 4,593,681 A * | 6/1986 | Soni | 600/102 |
| 4,698,057 A * | 10/1987 | Joishy | 604/176 |
| 4,959,055 A * | 9/1990 | Hillyer | 604/179 |
| 5,069,206 A * | 12/1991 | Crosbie | 128/207.17 |
| 5,176,649 A * | 1/1993 | Wakabayashi | 604/164.09 |
| 5,221,264 A | 6/1993 | Wilk et al. | |
| 5,263,939 A * | 11/1993 | Wortrich | 604/174 |
| 5,300,036 A | 4/1994 | Mueller et al. | |
| 5,391,156 A * | 2/1995 | Hildwein et al. | 604/174 |
| 5,397,335 A | 3/1995 | Gresl et al. | |
| 5,437,646 A | 8/1995 | Hunt et al. | |
| 5,512,053 A | 4/1996 | Pearson et al. | |
| 5,531,758 A | 7/1996 | Uschold et al. | |
| 5,556,411 A * | 9/1996 | Taoda et al. | 606/185 |
| 5,569,206 A | 10/1996 | Gorman, Jr. et al. | |
| 5,580,344 A | 12/1996 | Hasson | |

(Continued)

*Primary Examiner* — Jacqueline Johanas

(57) ABSTRACT

A surgical access assembly is presented including an expandable sleeve having a proximal end and a distal end, the proximal end including a first pair of wings and a second pair of wings outwardly extending away from the sleeve, the second pair of wings detachably connected to a distal end of the first pair of wings. The surgical access assembly also includes a cannula assembly having a cannula housing and a tubular member configured to be inserted through the expandable sleeve. The surgical access assembly further includes an adhesive member attached to an end point of each of the pair of second wings, the adhesive member of each of the pair of second wings facilitating attachment of the surgical access assembly to a skin surface.

9 Claims, 10 Drawing Sheets

(56) References Cited

U.S. PATENT DOCUMENTS

| | | | |
|---|---|---|---|
| 5,683,378 A * | 11/1997 | Christy | 606/1 |
| 5,752,938 A | 5/1998 | Flatland et al. | |
| 5,827,227 A | 10/1998 | DeLago | |
| 5,833,666 A * | 11/1998 | Davis et al. | 604/180 |
| 5,843,040 A | 12/1998 | Exline | |
| 5,868,714 A | 2/1999 | Danks | |
| 5,897,531 A * | 4/1999 | Amirana | 604/180 |
| 5,941,852 A | 8/1999 | Dunlap et al. | |
| 6,228,061 B1 | 5/2001 | Flatland et al. | |
| 7,749,198 B2 | 7/2010 | Smith | |
| 7,909,761 B2 * | 3/2011 | Banchieri | A61B 1/32 600/208 |
| 8,007,473 B2 | 8/2011 | Smith et al. | |
| 8,074,651 B2 * | 12/2011 | Bierman et al. | 128/207.17 |
| 8,109,910 B2 | 2/2012 | Zastawny et al. | |
| 8,162,890 B2 | 4/2012 | Amisar et al. | |
| 8,591,471 B1 * | 11/2013 | Marble | 604/174 |
| 8,636,701 B2 * | 1/2014 | Henry et al. | 604/178 |
| 8,961,548 B2 * | 2/2015 | Buser et al. | 606/174 |
| 9,067,013 B2 * | 6/2015 | Wright et al. | |
| 9,204,789 B2 * | 12/2015 | Wenchell | A61B 1/00154 |
| 2003/0208187 A1 | 11/2003 | Layer | |
| 2008/0033344 A1 * | 2/2008 | Mantell | 604/27 |
| 2008/0091144 A1 | 4/2008 | Moran et al. | |
| 2008/0103366 A1 * | 5/2008 | Banchieri | A61B 1/32 600/208 |
| 2008/0319387 A1 | 12/2008 | Amisar et al. | |
| 2009/0030443 A1 * | 1/2009 | Buser et al. | 606/185 |
| 2009/0209915 A1 * | 8/2009 | Zastawny et al. | 604/167.02 |
| 2009/0299302 A1 | 12/2009 | Lambert | |
| 2009/0326461 A1 * | 12/2009 | Gresham | 604/164.04 |
| 2010/0010449 A1 * | 1/2010 | Leibowitz et al. | 604/179 |
| 2010/0057010 A1 * | 3/2010 | Goransson | 604/164.04 |
| 2010/0069790 A1 | 3/2010 | Green | |
| 2010/0179483 A1 * | 7/2010 | Wright et al. | 604/180 |
| 2010/0292673 A1 | 11/2010 | Korogi et al. | |
| 2011/0071359 A1 | 3/2011 | Bonadio et al. | |
| 2011/0077597 A1 * | 3/2011 | Gresham | 604/164.03 |
| 2011/0087075 A1 * | 4/2011 | Wenchell | A61B 1/00154 600/235 |
| 2011/0224721 A1 * | 9/2011 | Edwards et al. | 606/213 |
| 2011/0259338 A1 | 10/2011 | Worley | |
| 2011/0264050 A1 * | 10/2011 | Henry et al. | 604/177 |
| 2011/0270041 A1 | 11/2011 | Heinrich | |
| 2011/0301552 A1 * | 12/2011 | Nakanishi | A61M 5/158 604/263 |
| 2012/0016394 A1 | 1/2012 | Bonadio et al. | |
| 2012/0041377 A1 * | 2/2012 | Haak | A61M 25/02 604/180 |
| 2012/0083661 A1 | 4/2012 | Rockrohr | |
| 2012/0116445 A1 * | 5/2012 | Rideout | A61B 17/3439 606/213 |
| 2012/0209078 A1 * | 8/2012 | Pribanic et al. | 600/208 |
| 2012/0247477 A1 | 10/2012 | Stephenson et al. | |
| 2013/0137933 A1 * | 5/2013 | Richard | 600/208 |
| 2014/0200410 A1 * | 7/2014 | Mantell | 600/208 |
| 2014/0371537 A1 * | 12/2014 | Marczyk et al. | 600/204 |

* cited by examiner

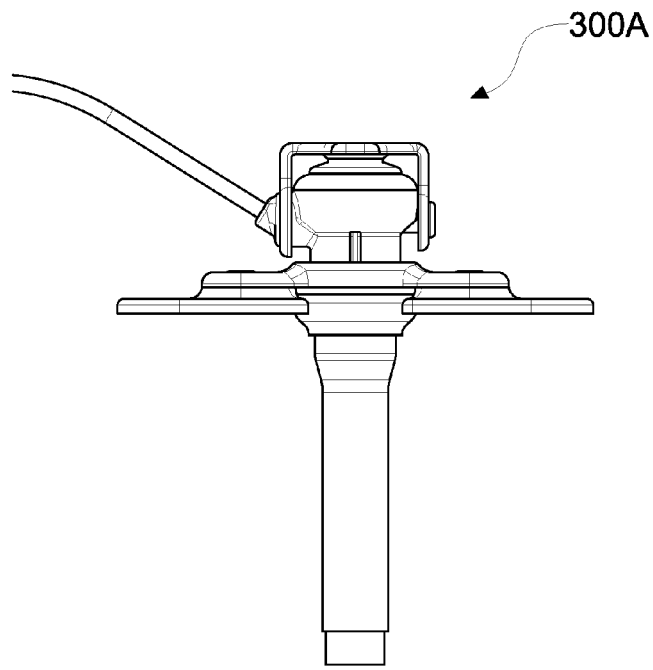
FIG. 3A
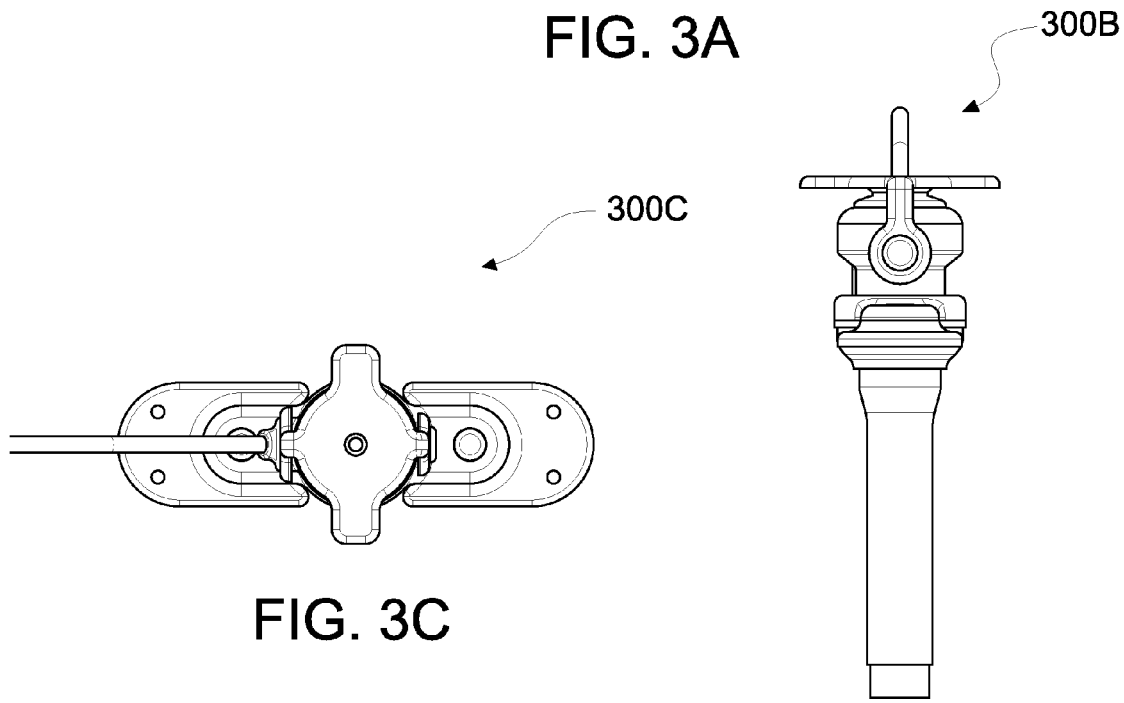
FIG. 3C
FIG. 3B

SURGICAL ACCESS ASSEMBLY INCLUDING ADHESIVE MEMBERS FOR SECURE ATTACHMENT TO SKIN SURFACES

CROSS-REFERENCE TO RELATED APPLICATIONS

This application claims the benefit of and priority to U.S. Provisional Patent Application No. 61/834,937, filed Jun. 14, 2013, the entire disclosure of which is incorporated by reference herein.

BACKGROUND

1. Technical Field

The present disclosure relates to a surgical access assembly and, more particularly, but not exclusively, relates to a surgical access assembly having adhesive members attached to a distal end of a pair of wings of a sleeve configured to cooperate with a cannula assembly.

2. Background of Related Art

Minimally invasive surgical procedures including both endoscopic and laparoscopic procedures permit surgery to be performed on organs, tissues and vessels far removed from an opening within the tissue. Laparoscopic and endoscopic procedures generally require that any instrumentation inserted into the body be sealed, i.e., provisions must be made to ensure that gases do not enter or exit the body through the incision as, for example, in surgical procedures in which the surgical region is insufflated. These procedures typically employ surgical instruments which are introduced into the body through a cannula. The cannula has a housing at a proximal end thereof in which a seal assembly is mounted. The seal assembly provides a substantially fluid tight seal about the instrument to preserve the integrity of the established pneumoperitoneum.

Minimally invasive procedures have several advantages over traditional open surgery, including less patient trauma, reduced recovery time, reduced potential for infection, etc. However, despite its recent success and overall acceptance as a preferred surgical technique, minimally invasive surgery, such as laparoscopy, has disadvantages. In particular, the insertion of the surgical instrument within the cannula has proven to be difficult in certain procedures, e.g., in procedures requiring extensive manipulation of the long narrow endoscopic instruments within a remote site. In addition, many conventional seal assemblies are not particularly well-adapted to receive a surgical instrument if it is inserted at an angle, thus resulting in damage to the seal assemblies. In addition, angulation and/or manipulation of instrumentation within the cannula often present difficulties with respect to maintaining seal integrity. Thus, there remains a need for an apparatus that may be used to guide a surgical instrument through a seal assembly in a more efficient and efficacious manner and for securely maintaining the seal assembly in its place.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

According to one aspect of the present disclosure, a surgical access assembly is provided. The surgical access assembly includes an expandable sleeve having a proximal end and a distal end, the proximal end including a first pair of wings and a second pair of wings outwardly extending away from the sleeve, the second pair of wings detachably connected to a distal end of the first pair of wings. The surgical access assembly also includes a cannula assembly including a cannula housing and a tubular member configured to be inserted through the expandable sleeve. The surgical access assembly further includes an adhesive member attached to an end point of each of the pair of second wings, the adhesive member of each of the pair of second wings facilitating attachment of the surgical access assembly to a skin surface.

In one exemplary embodiment, the first pair of wings is constructed from a rigid material, whereas the second pair of wings is constructed from a flexible material.

In another exemplary embodiment, the second pair of wings includes openings configured to receive sutures therethrough.

In yet another exemplary embodiment, the adhesive member of each of the pair of second wings defines an upper portion and a lower portion, the upper portion having a substantially oval shape.

In another exemplary embodiment, the lower portion is configured to include an adhesive break section for allowing the first and second pair of wings to be pulled away from the skin surface while the adhesive member of each of the pair of second wings remains flush with the skin surface.

In one exemplary embodiment, the proximal end of the sleeve includes a bayonet engagement feature configured to securely connect the sleeve to an introducer needle assembly. The introducer needle assembly includes a spring loaded hollow plunger at a proximal end thereof.

In another exemplary embodiment, the cannula housing of the cannula assembly includes a reducer seal. Additionally, the cannula assembly includes a tethered stop cock at a proximal end thereof.

In yet another exemplary embodiment, a distal end of the cannula assembly includes a balloon anchoring system.

According to another aspect of the present disclosure, a surgical access assembly is provided. The surgical access assembly includes a sleeve having a proximal end and a distal end, the proximal end including a first pair of projections constructed from a first material and a second pair of projections constructed from a second material, the first and second pair of projections outwardly extending away from the sleeve. The surgical access assembly also includes an adhesive member attached to an end point of each of the pair of second projections, the adhesive member of each of the pair of second projections facilitating attachment of the surgical access assembly to a skin surface.

In another aspect of the present disclosure, a method for performing a surgical procedure is provided. The method includes the steps of providing a sleeve having a proximal end and a distal end, the proximal end including a first pair of projections constructed from a first material and a second pair of projections constructed from a second material, the first and second pair of projections outwardly extending away from the sleeve and providing an adhesive member attached to an end point of each of the pair of second projections, the adhesive member of each of the pair of second projections facilitating attachment of the surgical access assembly to a skin surface.

Further scope of applicability of the present disclosure will become apparent from the detailed description given hereinafter. However, it should be understood that the detailed description and specific examples, while indicating preferred embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIGS. 3A-3C are a top view and side views of the surgical access assembly of FIG. 2, in accordance with the present disclosure;

Figure 1:
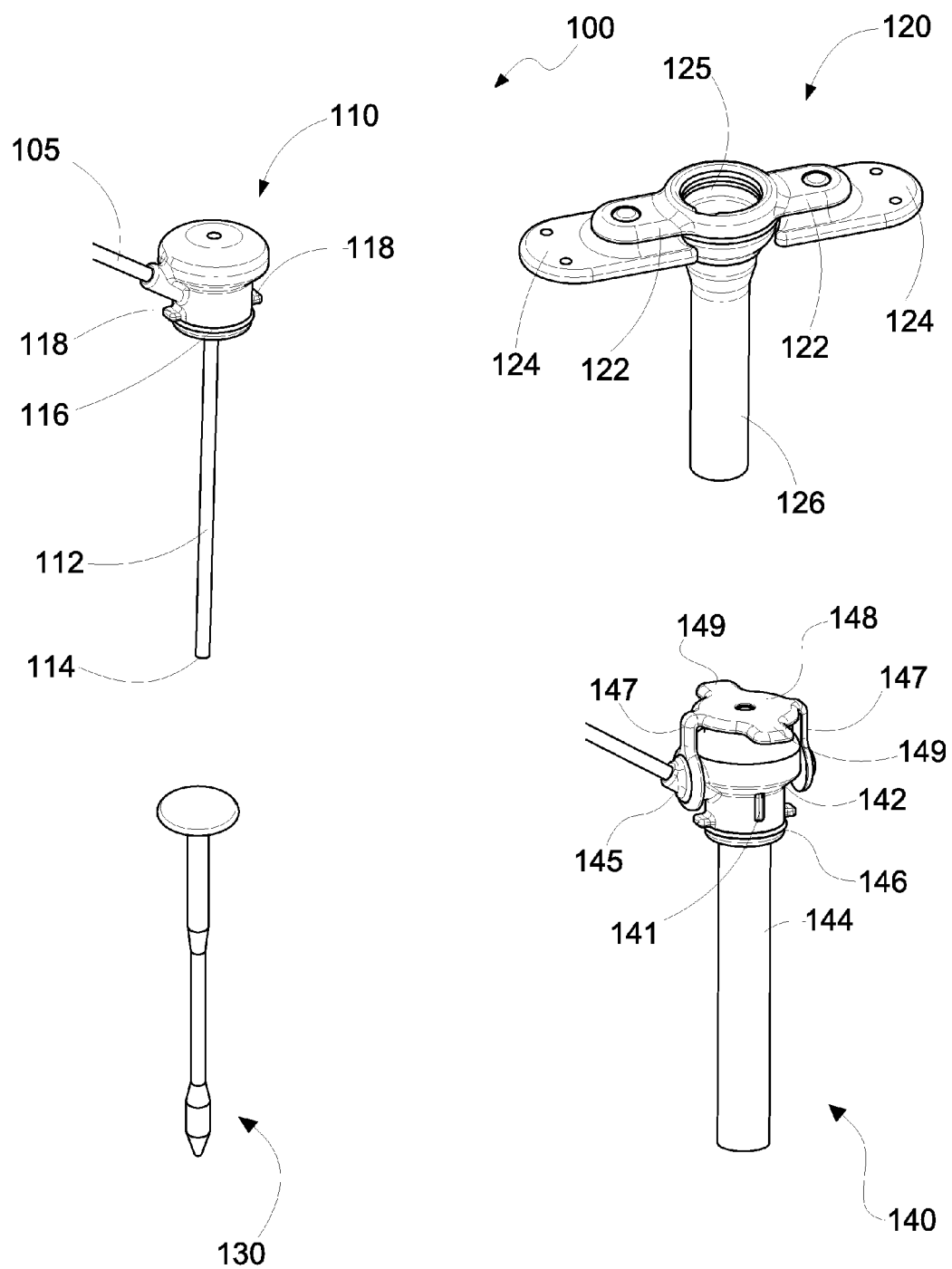
FIG. 1 is a perspective view, with parts separated, of a surgical access assembly in accordance with the principles of the present disclosure.

The figures depict preferred embodiments of the present disclosure for purposes of illustration only. One skilled in the art will readily recognize from the following discussion that alternative embodiments of the structures and methods illustrated herein may be employed without departing from the principles of the present disclosure described herein.

DETAILED DESCRIPTION

Particular embodiments of the present disclosure are described hereinbelow with reference to the accompanying drawings. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

For the purposes of promoting an understanding of the principles of the present disclosure, reference will now be made to the exemplary embodiments illustrated in the drawings, and specific language will be used to describe the same. It will nevertheless be understood that no limitation of the scope of the present disclosure is thereby intended. Any alterations and further modifications of the inventive features illustrated herein, and any additional applications of the principles of the present disclosure as illustrated herein, which would occur to one skilled in the relevant art and having possession of this disclosure, are to be considered within the scope of the present disclosure.

The access assembly contemplates the introduction and manipulation of various types of instrumentation adapted for insertion through a trocar and/or cannula assembly while maintaining a fluid tight interface about the instrumentation to preserve the atmospheric integrity of a surgical procedure from gas and/or fluid leakage. Specifically, the access assembly accommodates angular manipulation of the surgical instrument relative to the cannula housing axis. This feature of the present disclosure desirably minimizes the entry and exit of gases and/or fluids to/from the body cavity. Examples of instrumentation include clip appliers, graspers, dissectors, retractors, staplers, laser probes, photographic devices, endoscopes and laparoscopes, tubes, and the like. Such instruments will be collectively referred to herein as "instruments or instrumentation."

The word "exemplary" is used herein to mean "serving as an example, instance, or illustration." Any embodiment described herein as "exemplary" is not necessarily to be construed as preferred or advantageous over other embodiments. The word "example" may be used interchangeably with the term "exemplary."

Embodiments of the presently disclosed apparatus will now be described in detail with reference to the drawings, in which like reference numerals designate identical or corresponding elements in each of the several views. As used herein, the term "distal" refers to that portion of the tool, or component thereof which is farther from the user while the term "proximal" refers to that portion of the tool or component thereof which is closer to the user.

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

For exemplary purposes, the access apparatus will be described in terms of a cannula assembly, which is adapted for introduction, typically utilizing a trocar, within the abdominal cavity during a laparoscopic surgical procedure. However, it is appreciated that the access apparatus may be any apparatus suitable for introduction and passage of surgical objects into underlying tissue including, e.g., catheters, trocar assemblies, endoscopic portals, hand access devices, etc., through an incision or through a natural body opening.

Figure 2:
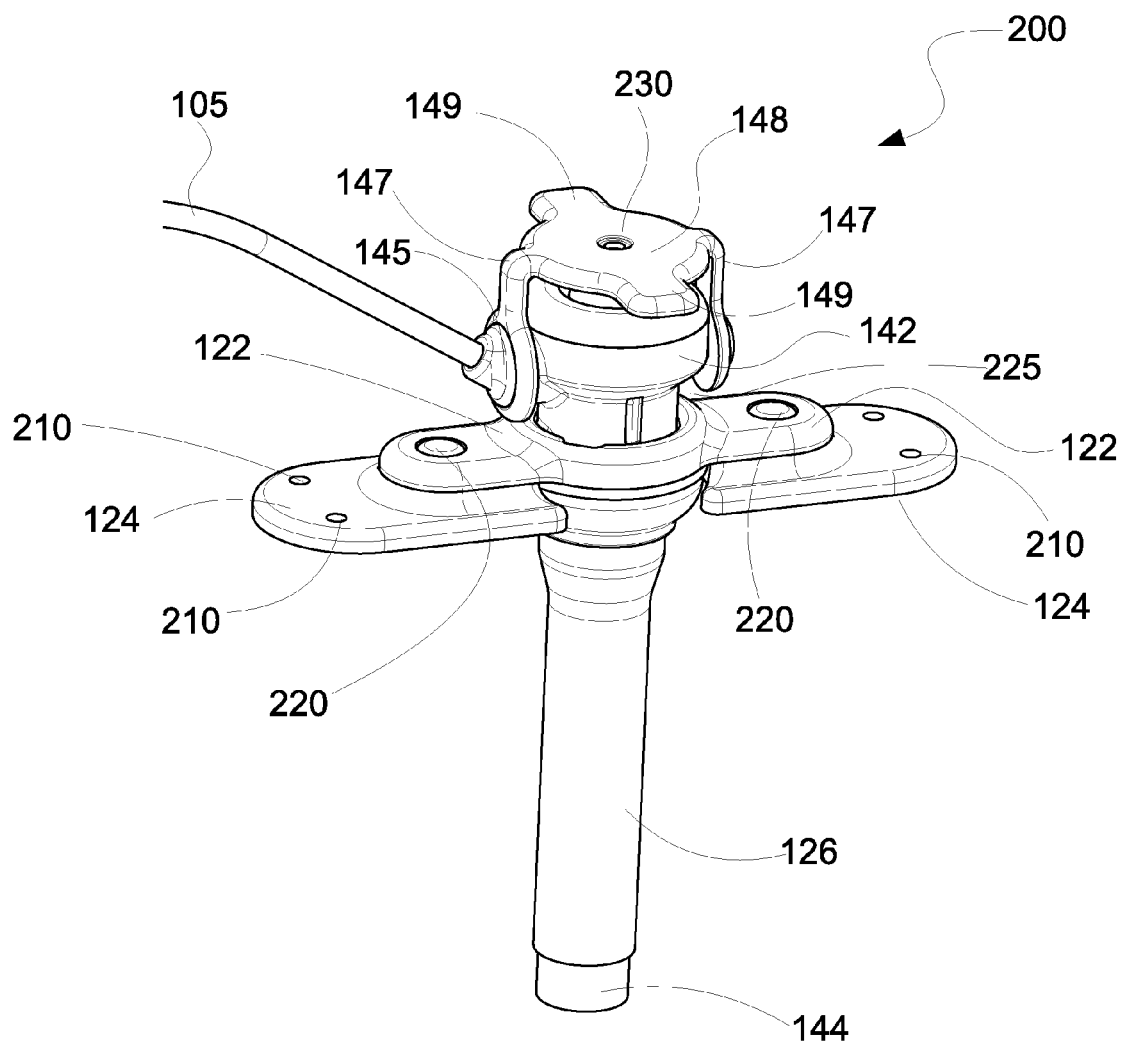
FIG. 2 is a perspective view of the assembled surgical access assembly of FIG. 1, in accordance with the present disclosure.
Figure 4:
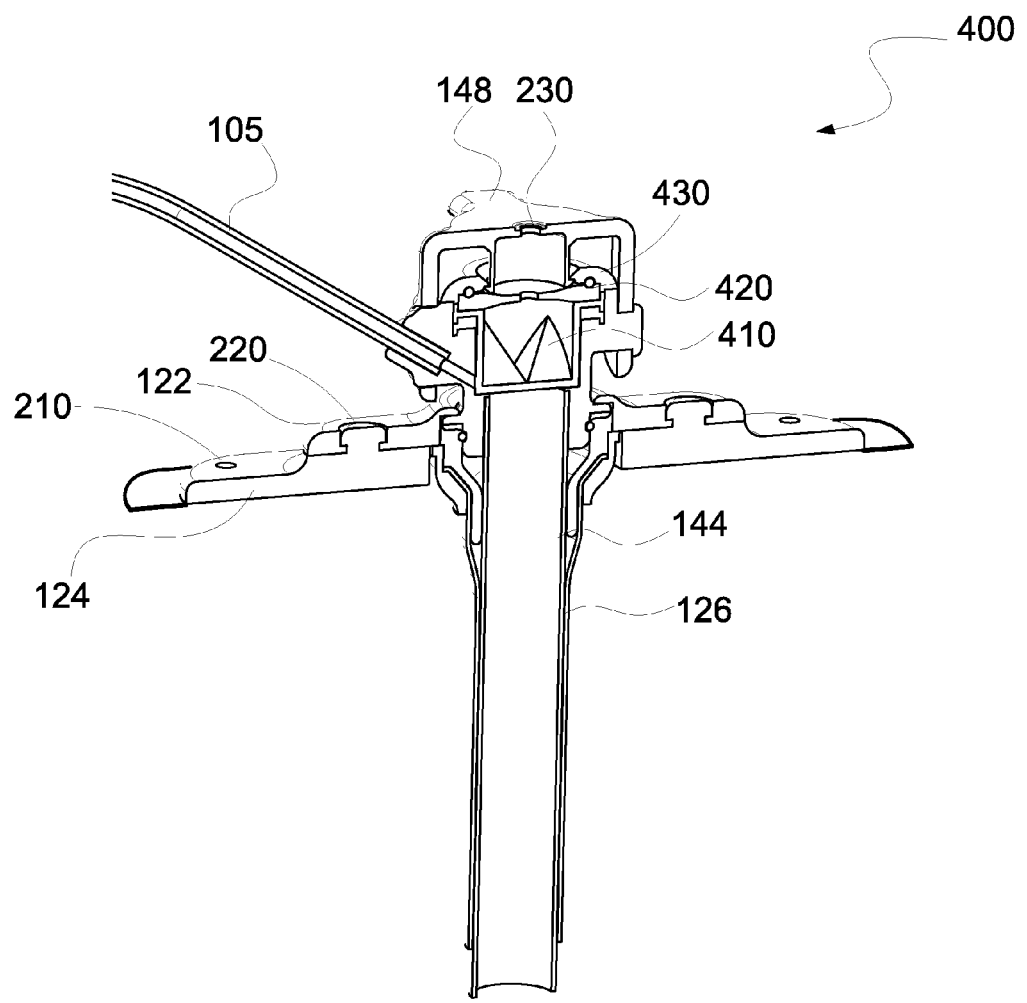
FIG. 4 is a cross-sectional view of a portion of the surgical access assembly of FIG. 2, in accordance with the present disclosure.

Referring now to the drawings, in which like reference numerals identify identical or substantially similar parts throughout the several views, FIG. 1 illustrates a surgical access assembly 100, with parts separated. Referring to FIG. 1, there are four main parts to the surgical access assembly 100. The parts are an introducer needle 110, a sleeve 120, an obturator 130, and a cannula assembly 140. The cannula assembly 140 may include a reducer seal 148. FIG. 2 illustrates the assembled surgical access assembly 200 of FIG. 1, whereas FIGS. 3A-3C illustrate top and side views of the surgical access assembly of FIG. 1. FIG. 4 is a cross-sectional view 400 of FIG. 2. FIGS. 1-4 will be described concurrently herewith.

The introducer needle 110 has a spring loaded hollow plunger 114. The needle 112 has two small protrusions 118 configured to engage the sleeve 120, discussed below. The insufflation needle 110 also has tubing 105 adapted and dimensioned for abdominal cavity insufflation. The insufflation is performed through the hollow plunger 114, which includes openings at a distal end thereof. Attaching the tubing 105 to the side of the needle 112 allows the surgeon to push the needle 112 through its flat proximal end during insertion. The O-ring 116 on the body of the needle 112 aids to seal the needle 112 to the sleeve 120.

The sleeve 120 has a pair of first wings 122. The pair of first wings 122 is constructed from a rigid material. The sleeve 120 also includes a pair of second wings 124. The pair of second wings 124 is attached to end points or areas or sections of the pair of first wings 122. The pair of second wings 124 is constructed from a flexible material. The pair of first wings 122 is attached to the pair of second wings 124 via connectors 220 (see FIG. 2). The second pair of wings 124 includes openings 210 (see FIG. 2) configured to receive sutures therethrough, thus suturing the sleeve 120 to the skin of a patient. Thus, the sleeve 120 includes two components. That is, a first pair of wings 122 and a second pair of wings 124, where the second pair of wings 124 is detachably connected to the first pair of wings 122 via connectors 220. The second pair of wings 124 may be detached at any time by the surgeon to facilitate fixation. Additionally, a proximal end of the sleeve 120 defines a solid ring formed integrally with the pair of first wings 122.

Figure 9:
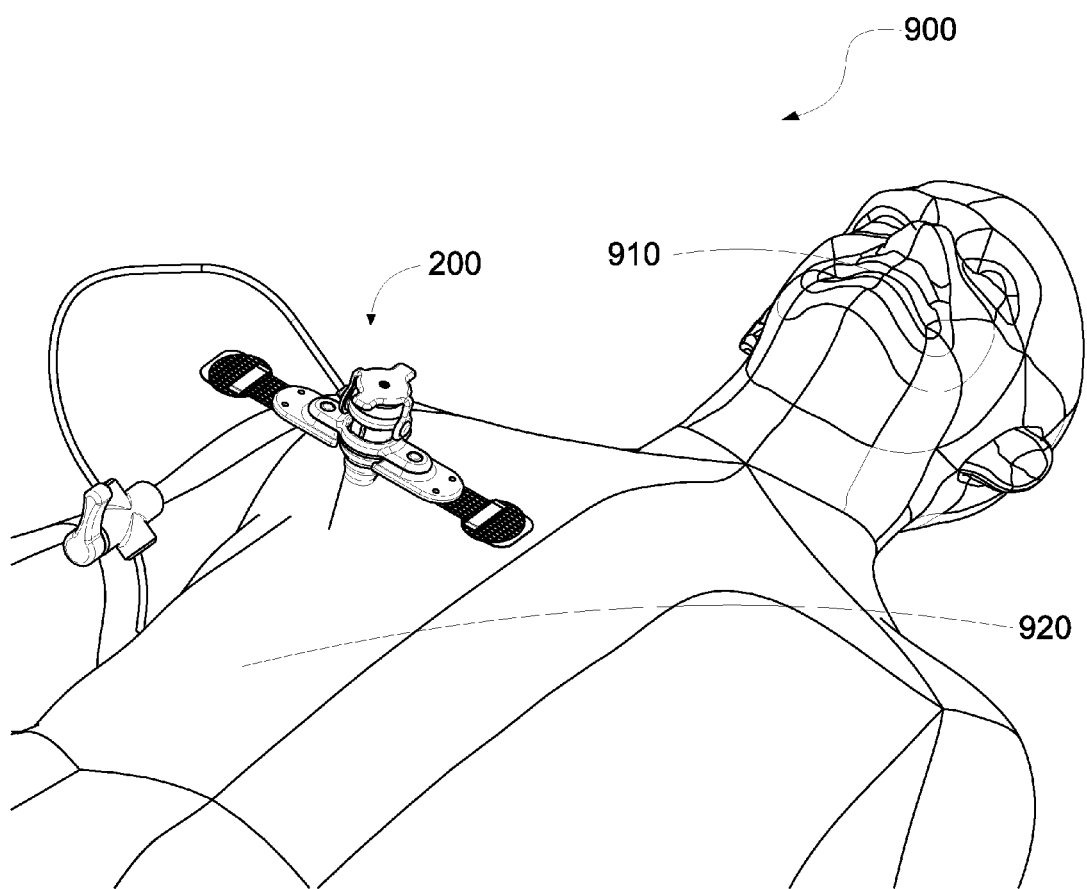
FIG. 9 is a perspective view of the surgical access device of FIG. 2 inserted into an abdomen of a person, in accordance with the present disclosure.

The first and second pair of wings 122, 124 provide support for the fingers of a surgeon to aid in the insertion of the sleeve 120 to an abdominal wall of a patient (see FIG. 9). The second pair of wings 124 minimizes unnecessary pressure on the abdominal wall of the patient when the cannula assembly 140, discussed below, is rotated. By removing the second pair of wings 124, the surgeon has the option to further minimize the footprint of the surgical access assembly 100. The sleeve 120 may be constructed from an expandable material covered with a Mylar thin sheath. The sheath (not shown) may help retain the shape of the sleeve 120 and minimize friction between the sleeve 120 and the abdominal wall of the patient during insertion of the introducer needle 110. The wings 122, 124 may also be referred to as projections throughout the specification.

The distal end of the sleeve 120 includes a tubular member 126, whereas the proximal end of the sleeve 120 includes a bayonet engagement feature 125. The engagement feature 125 securely connects the sleeve 120 to the needle 112 of the introducer needle 110 during insertion and insufflation.

The cannula assembly 140 includes a cannula housing 142 and a tubular member 144. The cannula assembly 140 has tubing 145 that increases the placement flexibility. The tubing 145 is attached to the cannula housing 142 via the reducer seal 148, described below. Referring to FIG. 4, the cannula assembly 140 includes a duckbill seal 410 and a seal 420. The seal 420 may be a 5 mm seal. However, one skilled in the art may contemplate any size for the seal 420. Referring back to FIG. 1, the O-ring 146 helps maintain proper engagement between the cannula assembly 140 and the sleeve 120. The cannula assembly 140 is inserted into the sleeve 120, as shown in FIG. 2, where a connection or attachment 225 is enabled at a proximal end of the sleeve 120.

The cannula assembly 140 may also include a reducer seal 148 positioned at a proximal end thereof. The reducer seal 148 expands the range of instruments which can be accommodated by the cannula assembly 140 by accepting surgical instruments from, for example, 2 mm to 3.5 mm in diameter. The surgical instruments may be accepted through opening 230 (see FIG. 2). The reducer seal 148 is attached to the cannula assembly 140 with two pivots 147. The surgeon need only grab the reducer seal 148 using the flaps 149, rotate the reducer seal by 90 degrees, and push it down toward the cannula assembly 140 entrance (i.e., proximal end of the cannula assembly 140). Additionally, as shown in FIG. 4, a detent feature 430 may help align the reducer seal 148 with the entrance of the cannula assembly 140. Moreover, two protrusions or extensions or ribs 141, at opposed ends of the cannula housing 142 stabilize the reducer seal 148 to the cannula housing 142. It is also contemplated that instead of protrusions or extensions, the element 141 may be a recess or a slot that cooperates with the sleeve 120. FIG. 3A depicts a top view 300A, whereas FIGS. 3B and 3C depict side views 300B, 300C of the cannula assembly 140 inserted into the sleeve 120.

Moreover, it is contemplated that the first pair of wings 122 are smaller than the second pair of wings 124. It is contemplated that the pair of wings 122, 124 form a substantially semi-circular shape. The second pair of wings 124 may be substantially twice the size of the first pair of wings 122. The first pair of wings 122 may be constructed from a first material, whereas the second pair of wings 124 may be constructed from a second material, the first material being different than the second material. The first pair of wings 122 may be constructed from the same material used to form the cannula housing 142. It is contemplated that either the first material or the second material are transparent. It is also contemplated that the cannula housing 142 is transparent.

Regarding FIGS. 1-4, it is contemplated that the introducer needle 110, the sleeve 120, the obturator 130, and the cannula assembly 140 are optimized for infant and child anatomy. The overall size of the cannula assembly is contemplated to be much smaller than regular cannula assemblies in order to be used with children and infants.

To assure reliable performance of the cannula assembly 140, it is contemplated that the cannula assembly is attached to an abdominal wall of a patient (see FIG. 9). The attachment or fixation should be strong enough to resist the friction force pulling the cannula assembly 140 out when the surgeon slides the surgical instrument along the cannula housing axis and through the opening 230 of the access assembly 200 (see FIG. 2). At the same time, the cannula assembly 140 has the freedom to rotate about a pivot point to allow surgical instruments to reach the surgical site. Several method may be used with the cannula assembly 140 described herein to allow for such freedom to rotate. For example, threads or barbs or anchoring systems or balloons or adhesives, or sutures may be used. FIGS. 5A-9, described below, illustrate exemplary adhesive pads or members, whereas FIGS. 10A-10C, described below, illustrate exemplary balloon anchoring systems. Additionally, when proposing fixation systems for infants, the characteristics of the abdominal wall of the infant or child must be taken into consideration. In particular, even though the abdominal wall is relatively strong, it is quite thin, such that cannula assemblies with barbs may not provide adequate fixation or attachment, and may cause injury to the infant or child. As a result, the openings 210 (see FIG. 2) on opposed ends of the second pair of wings 124 provide for fixation or attachment by suturing that may be more appropriate for infants and children. Moreover, adhesive pads or adhesive members may be used for fixation or attachment purposes, as described below with reference to FIGS. 5A-9.

Figure 5A:
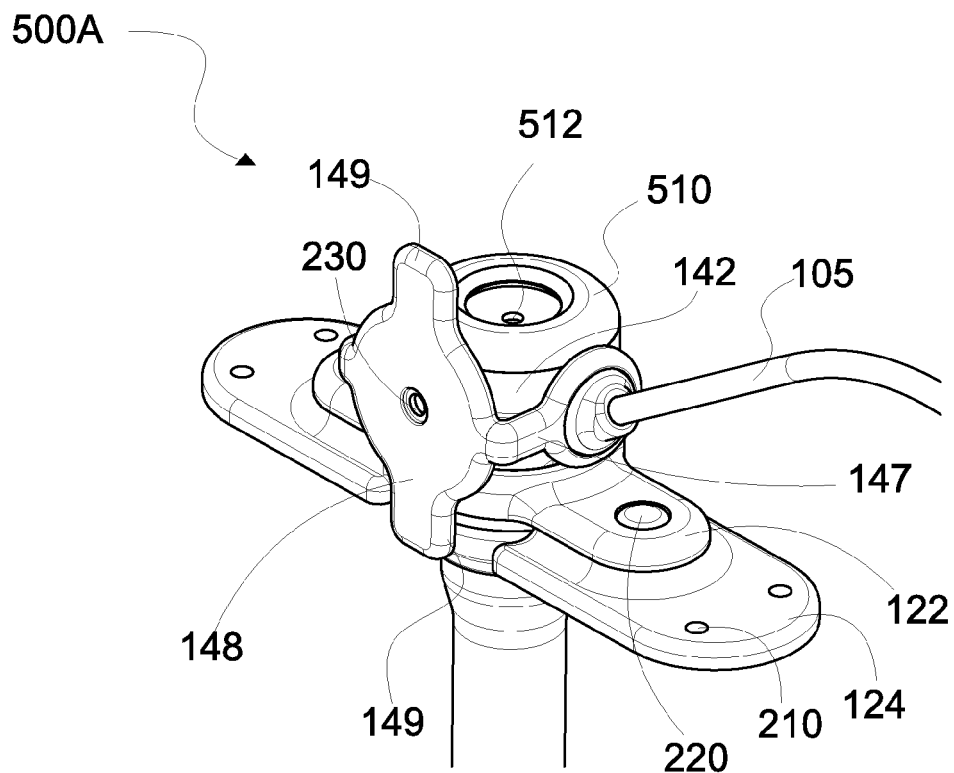
FIGS. 5A-5B are perspective views of a reducer seal moved from a first position to a second position while attached to a top portion of the surgical access assembly, in accordance with the present disclosure.
Figure 5B:
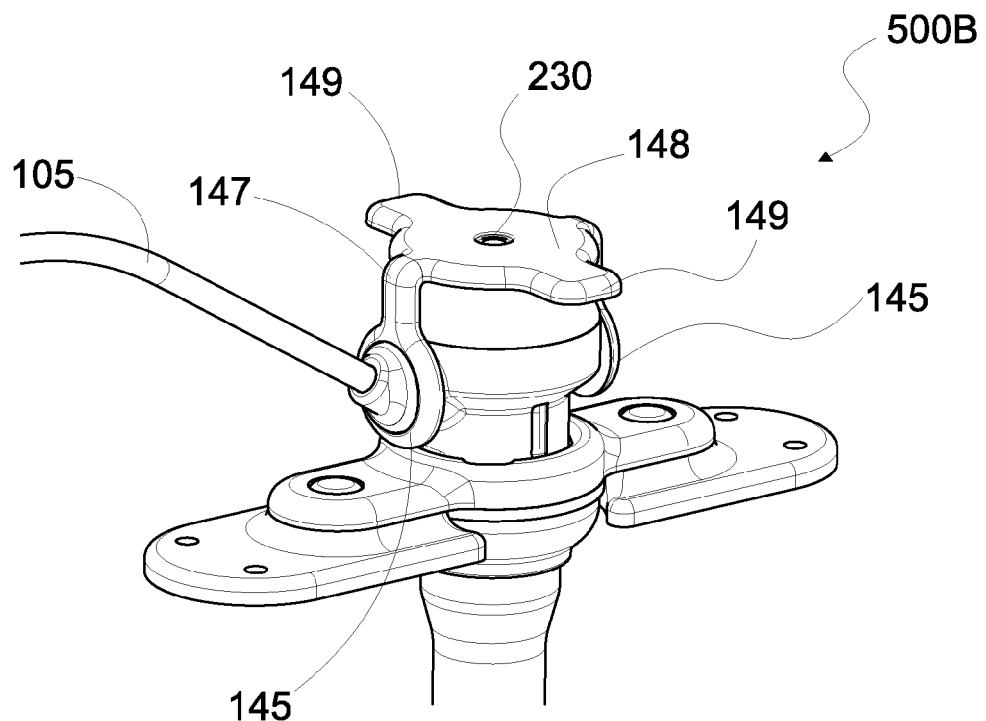

FIGS. 5A-5B are perspective views of a reducer seal 148 moved from a first position 500A to a second position 500B, while attached to a top portion of the surgical access assembly, in accordance with the present disclosure.

In FIG. 5A, the reducer seal 148 is provided to accommodate a first surgical instrument having a predetermined diameter typically smaller than that of other surgical instruments used through cannula assembly 140. Reducer seal 148 incorporates reducer bore 512 configured to receive first surgical instrument at the proximal end 510 of the cannula housing 142. Reducer seal 148 is movably mounted on cannula assembly 140. Specifically, reducer seal 148 is pivotally mounted on pivot pins 145 extending from the cannula body 142. A pair of distally extending legs 147 extend distally from a top portion of the reducer seal 148. Circular central portion 512 is provided with a downwardly extending lip. Preferably, reducer seal 148 is formed of a substantially elastomeric material such that reducer seal 148 can be stretched up and away from proximal end 510 of cannula housing 142 when the reducer seal 148 is moved from the closed to the open position. Additionally, the elastomeric nature of reducer seal 148 allows reducer seal 148 to be relatively unobtrusive when in the open position.

Figure 6:
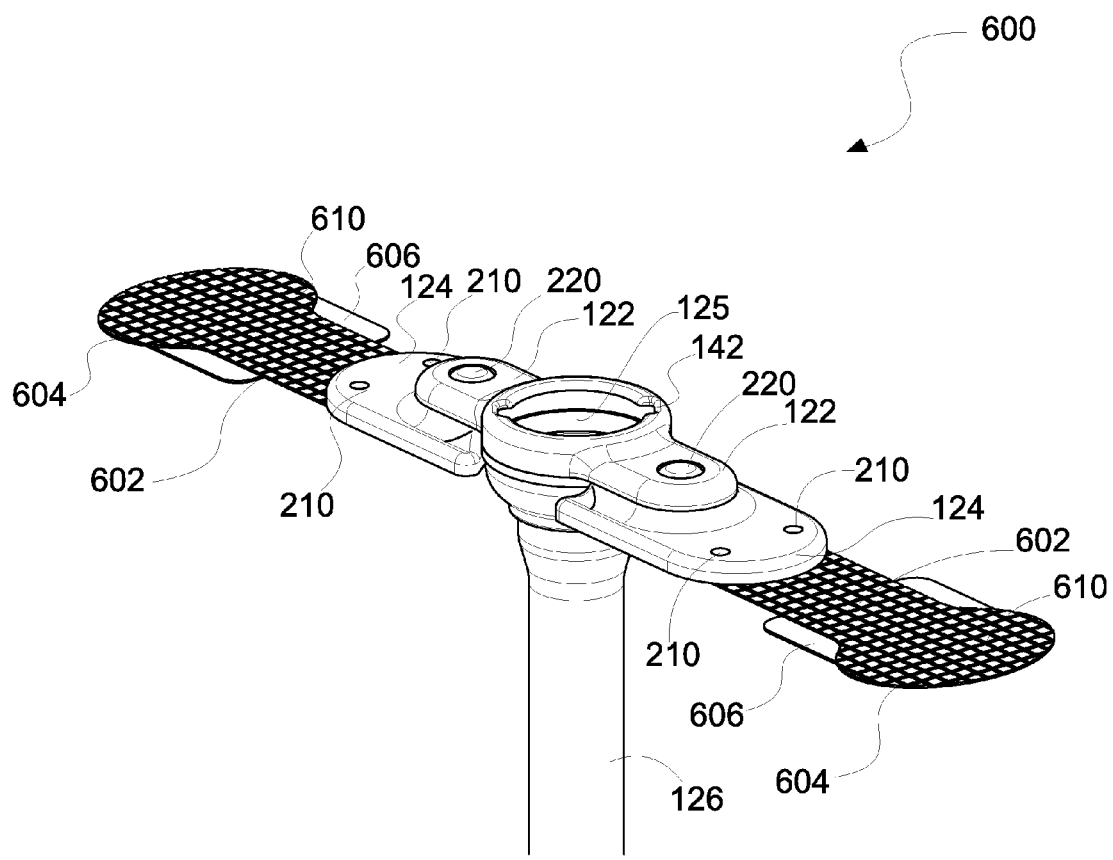
FIG. 6 is a perspective view of a surgical access assembly having adhesive members attached to end points or areas or sections of the second wings, in accordance with a first embodiment of the present disclosure.

FIG. 6 is a perspective view of a surgical access assembly 600 having an adhesive member 610 attached to distal end points or areas or sections of the wings 124, in accordance with a first embodiment of the present disclosure.

The surgical access assembly 600 includes an adhesive 610 attached to distal end points or areas or sections of each of the second wings 124. The adhesive member 610 of each of the pair of second wings 124 defines an upper portion 604 and a lower portion 602, the upper portion 604 having a substantially oval shape. One side of the adhesive portion 610 may include a release liner 606. The adhesive portion 610 may be attached underneath the pair of second wings 124. The width of the lower portion 602 may be substantially equal to the width of the second wings 124. The width of the upper portion 604 may be larger than the width of the second wings 124. It is also contemplated that the adhesive members 610 extend a distance greater than the full length of each of the second wings 124. In other words, the length of the adhesive members 610 is greater than the length of either the first wing 122 or the second wing 124. One skilled in the art may contemplate a plurality of different dimensional configurations for the first wings 122, the second wings 124, and the adhesive members 610.

Once the release liners 606 are removed, the adhesive members 610 are configured to attach to the skin of a patient (e.g., a child or an infant). The adhesive member 610 is strong enough to securely attach to the patient without being inadvertently removed. It is contemplated that the adhesive strength of the adhesive member 610 is strong enough to withstand inadvertent forces applied thereto or unexpected movements of the patient. The adhesive member 610 is configured to secure the sleeve 120 in place while the cannula assembly 140 is inserted therethrough (see FIGS. 1 and 2), as well as when surgical instruments are inserted through the cannula assembly 140. It is contemplated that rotational movement of the cannula assembly 140 would not affect the adhesiveness of the adhesive member 610 to the skin of the patient. It is also contemplated that any forces applied to the sleeve 120 would not dislodge the adhesive member 610 from its initial placement on the skin of the patient. It is contemplated that the surface area (lower portion) of the adhesive members 610 is greater than the surface area of the first and second pair of wings 122, 124 in order to properly and securely position the surgical access assembly 600 on or about the patient. It is also contemplated that an upper portion of the adhesive member 610 includes a grid-like pattern.

Figure 7:
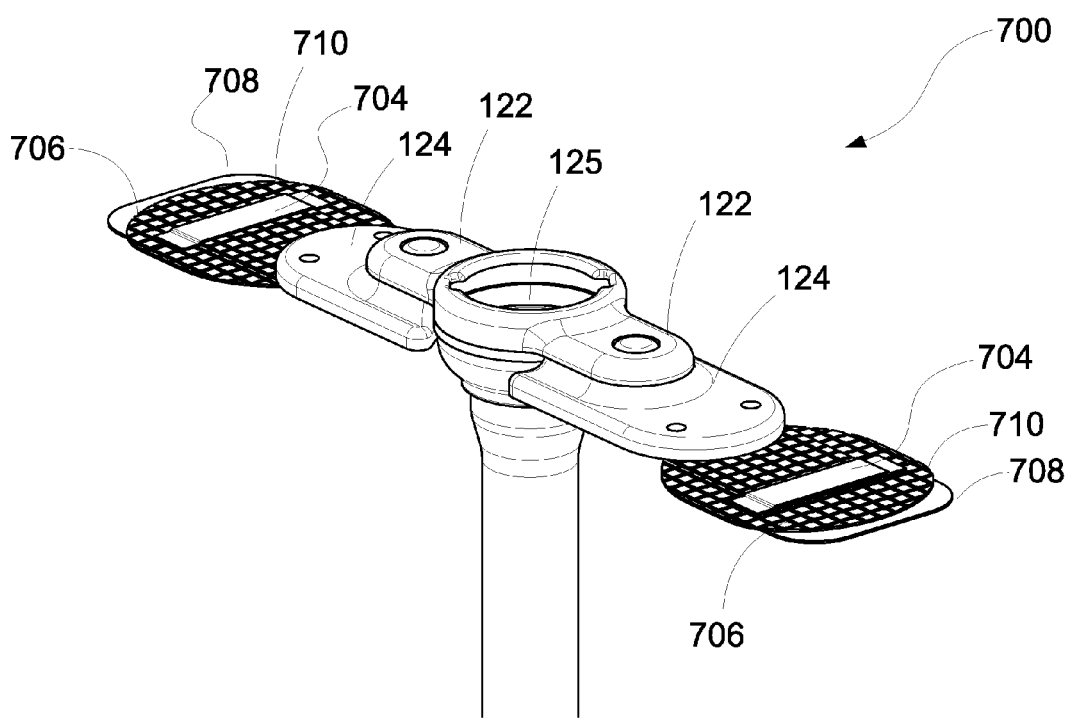
FIG. 7 is a perspective view of a surgical access assembly having adhesive members attached to end points or areas or sections of the second wings, the adhesive members including an adhesive break section, in accordance with a second embodiment of the present disclosure.

FIG. 7 is a perspective view of the surgical access assembly 700 having an adhesive member 710 attached to distal end points or areas or sections of the wings 124, in accordance with a second embodiment of the present disclosure.

The surgical access assembly 700 includes an adhesive 710 attached to distal end points or areas or sections of each of the second wings 124. In one embodiment, the adhesive member 710 need not define upper and lower portions as in FIG. 6. Instead, the adhesive member 710 defines one single substantially circular or oval surface area 706. One side of the adhesive portion 710 may include a release liner 708. The adhesive portion 710 may be attached underneath the pair of second wings 124. In contrast to FIG. 6, in FIG. 7, the upper part of the adhesive member 710 includes an adhesive break section 704 for allowing the first and second pair of wings 122, 124 to be pulled away from the skin surface of the patient while the adhesive member 710 of each of the second pair of wings 124 remains flush with the skin surface. Stated differently, a portion of the adhesive member 710 may remain flush with the skin, while the surgeon temporarily lifts the surgical access assembly 700, as better shown with reference to FIGS. 8A and 8B.

Figure 8A:
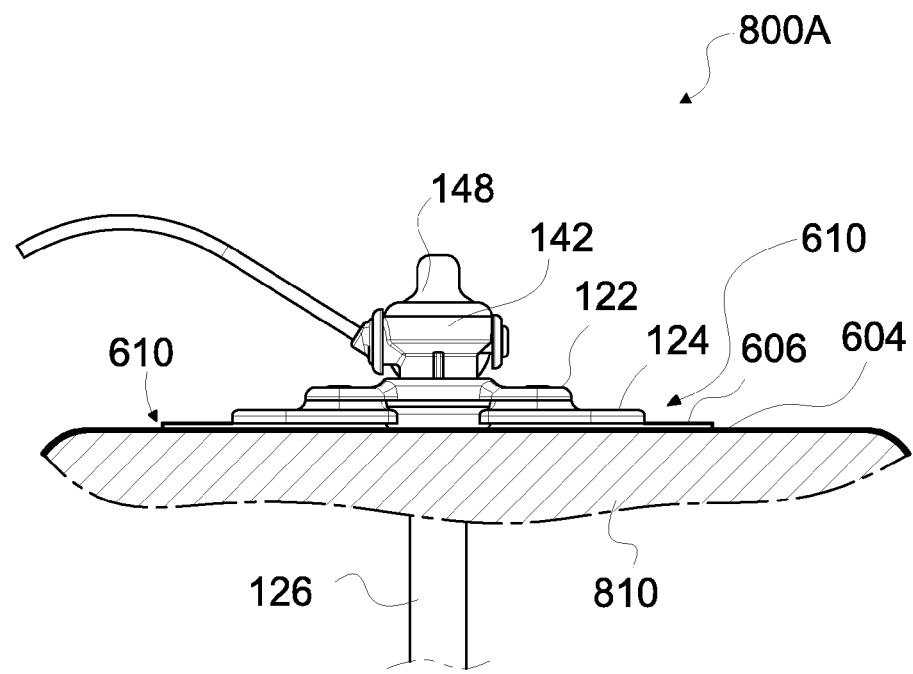
FIG. 8A is a side view of the surgical access device of FIG. 6, in accordance with an embodiment of the present disclosure.
Figure 8B:
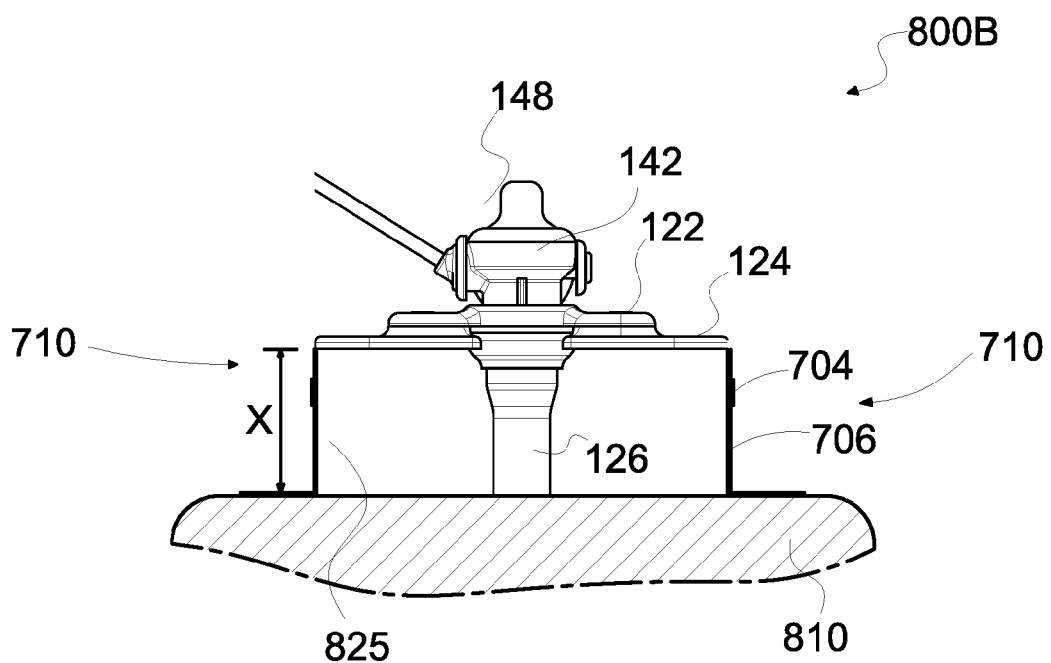
FIG. 8B is a side view of the surgical access device of FIG. 7, in accordance with an embodiment of the present disclosure.

FIG. 8A is a side view 800A of the surgical access device of FIG. 6, in accordance with an embodiment of the present disclosure, whereas FIG. 8B is a side view 800B of the surgical access device of FIG. 7, in accordance with an embodiment of the present disclosure.

In FIG. 8A, the adhesive member 610 remains flush with the skin of the patient at all times. In other words, the upper portion 604 and the lower portion 606 both remain flush with the skin 810 of the patient while the surgeon inserts surgical instruments through the cannula assembly 140 and performs surgical procedures. This configuration allows for fixation of the access assembly to the skin 810 of the patient via adhesive members 610.

In contrast, in FIG. 8B, at least a portion of the adhesive members 710 need not remain flush with the skin 810 of the patient at all times. In other words, the surgeon can manipulate the adhesive break section 704, such that the cannula assembly 140 is lifted from the skin surface of the patient (distance "X" or element 825). For example, the cannula assembly 140 may be lifted a few millimeters or a few inches (e.g., 1-3 inches). This allows for more maneuverability of the cannula assembly and the surgical instruments inserted therethrough. In particular, the cannula assembly 140 may be slightly rotated, while remaining in a substantially secure position (in a substantially vertical place) with respect to the skin 810 of the patient. Thus, the cannula assembly 140 or access assembly 200 has a sufficient degree of freedom to move or shift or rotate, even when the access assembly 200 is adhered to the skin 810 of the patient via the adhesive members or pads 710. Stated differently, there is a direct relationship between the need for mobility of the access assembly 200 and the need to fixate or securely attach the access assembly 200 at a desired surgical site. This delicate balance is achieved by a combination of adhesive members and adhesive break sections. Moreover, the configuration of FIG. 8B may be referred to as a zigzag configuration or a "Z" configuration because the adhesive member 710 forms a "Z" shape as it is lifted off the skin of the patient to enable rotational or spherical motion by the surgeon, while constantly maintaining some degree of fixation to the skin of the patient.

FIG. 9 is a perspective view 900 of the surgical access device 200 of FIG. 2 inserted into an abdomen 920 of a person 910, in accordance with an embodiment of the present disclosure.

Figure 10A:
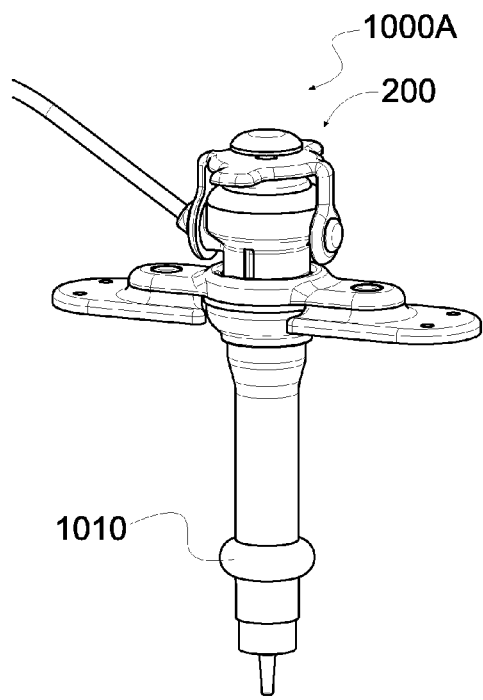
FIGS. 10A-10C are perspective views of a surgical access assembly having various balloon anchoring mechanisms, in accordance with another embodiment of the present disclosure.
Figure 10B:
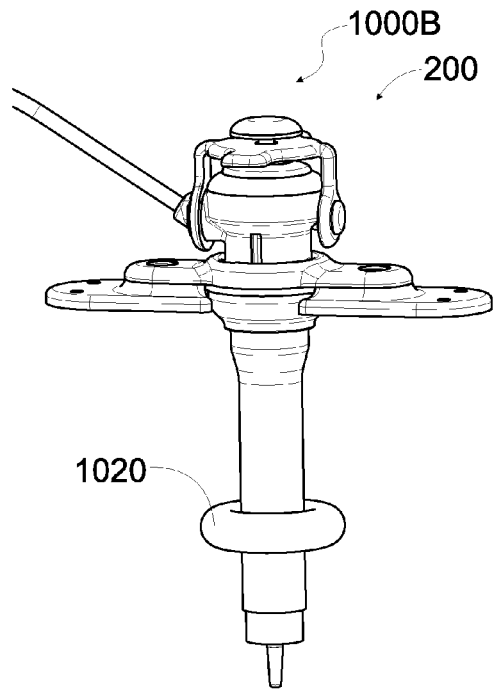
Figure 10C:
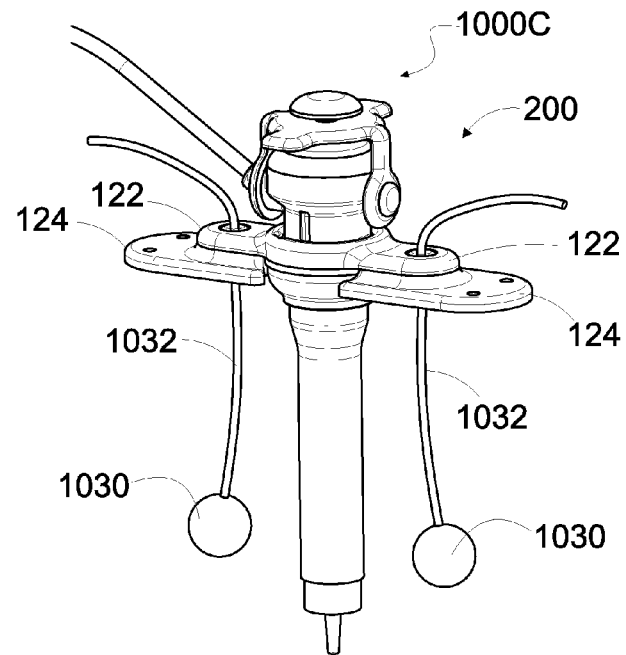

FIGS. 10A-10C are perspective views 1000A, 1000B, 1000C of a surgical access assembly having various balloon anchoring mechanisms, in accordance with another embodiment of the present disclosure.

Balloon systems may be combined with the expandable sleeve 120 to provide for additional fixation. The balloons may be used in combination or in conjunction with the adhesive members or pads described in FIGS. 5A-9. However, it is contemplated that the balloons of FIGS. 10A-10C may be used in place of the adhesive members.

In use, after the sleeve 120 is placed through the surgical site, the balloons could be inflated to provide for fixation. The balloons could be created by selectively bonding the outer layer on the expandable sleeve 120, thus leaving a ring or some other shape section un-adhered towards the distal end of the sleeve 120. FIG. 10A depicts a ring 1010 of a first size, whereas FIG. 10B depicts a ring 1020 of a second size, the second size being greater than the first size. FIG. 10C depicts a ball and string mechanism. For example, a ball 1030 may be attached to a string 1032. The string 1032 may be attached to the access assembly 200 via the openings of the first pair of wings 122. Of course, one skilled in the art may contemplate a plurality of different balloon mechanisms for fixing the access assemblies of the exemplary embodiments of the present disclosure to the patient. Thus, any type of balloon system may be attached or tethered towards the proximal end of the sleeve 120. The surgeon could adjust how far the balloons are deployed through the abdominal wall by changing the amount of tubing that extends out of the patient. If the cannula assembly 140 starts to migrate out of the wound, the tethers will become taut and the outward migration of the cannula assembly 140 is stopped. Additionally, in order to minimize the opportunity for loss of pneumoperitoneum, the tether/inflation tubes could be formed of different cross-sectional shapes.

Therefore, in summary, the expandable sleeve helps to minimize entrance wound sizes, and, thus, minimizes pain, scars, and risks of developing hernias. In addition to minimizing the cannula assembly by 75%, several additional elements provide the cannula assembly with the capability to be used with children and infants. These elements are the tethered stop cocks, the first and second pair of detachable wings or projections, the openings on the first and second pair of wings configured to receive sutures, the reducer seal, the smaller shaft length customized to the size of children and infants, the ergonomics of the insufflation needle, the fixation of the access assembly via the adhesive pads or members, and the chamfered entrance of the cannula assembly. The cannula assembly of the exemplary embodiments of the present disclosure may accept surgical instruments between, for example, 2 and 5 mm diameters, although other sizes and ranges are contemplated by one skilled in the art. The diameter choice allows the surgeon not only to use available scopes, but also allows the surgeon to insert the needle through the cannula to suture the wound laparoscopically if needed.

The advantages of the present disclosure include the fact that the sleeve, the cannula assembly, and the needle lengths are optimized for infant and small child anatomy. The insufflation needle has a tethered stop cock to improve the gripping stability and finger position when the surgeon inserts the needle with the sleeve into the abdominal wall of the patient. Further advantages include the sleeve having soft wings to minimize patient discomfort, having openings to facilitate fixation by suturing, having tethered adhesive pads to facilitate fixation, having detachable wings to minimize its footprint when adhesive pads are removed, and having a bayonet engagement with the needle for secure engagement during insertion. Further advantages include the cannula assembly having a chamfered entrance to help with insertion of surgical instruments, having a cannula housing minimized by up to 75% to prevent interference with other surgical instruments, having a tethered stop cock to prevent interference with the patient and other surgical instruments, having a reducer seal attached to its pivot points, the cannula body or cannula housing having at least two ribs which serve as docking stops for the reducer seal when not in use, and having a duckbill seal, as well as a 5 mm seal. Moreover, further advantages include the needle and the cannula assemblies each having an O-ring to insure leak proof performance, as well as a balloon anchoring system for replacing or enhancing the functionality of the adhesive pads or members.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

What is claimed is:

1. A surgical access assembly, comprising:
   an expandable sleeve having a proximal end and a distal end, the proximal end including a first pair of wings and a second pair of wings outwardly extending away from the sleeve, the second pair of wings detachably connected to a distal end of the first pair of wings, the distal end of the expandable sleeve including a tubular member;
   a cannula assembly including a cannula housing and a tubular member configured to be insertable through the expandable sleeve; and
   an adhesive member attached to an end point of each of the pair of second wings, the adhesive member of each of the pair of second wings facilitating attachment of the surgical access assembly to a skin surface;

wherein the first pair of wings is constructed from a rigid material and the second pair of wings is constructed from a flexible material.

2. The surgical access assembly according to claim 1, wherein the second pair of wings includes openings configured to receive sutures therethrough.

3. The surgical access assembly according to claim 1, wherein the adhesive member of each of the pair of second wings defines an upper portion and a lower portion, the upper portion having an oval shape.

4. The surgical access assembly according to claim 3, wherein the lower portion is configured to include an adhesive break section for allowing the first and second pairs of wings to be pulled away from the skin surface while the adhesive member of each of the pairs of first and second wings remains flush with the skin surface.

5. The surgical access assembly according to claim 1, wherein the proximal end of the sleeve includes a bayonet engagement feature configured to securely connect the sleeve to an introducer needle assembly.

6. The surgical access assembly according to claim 5, wherein the introducer needle assembly includes a spring loaded hollow plunger at a proximal end thereof.

7. The surgical access assembly according to claim 1, wherein the cannula housing of the cannula assembly includes a reducer seal.

8. The surgical access assembly according to claim 1, wherein the cannula assembly includes a tethered stop cock at a proximal end thereof.

9. The surgical access assembly according to claim 1, wherein a distal end of the cannula assembly includes a balloon anchoring system.

* * * * *